United States Patent [19]

Beck et al.

[11] Patent Number: 4,681,562
[45] Date of Patent: Jul. 21, 1987

[54] METHOD AND APPARATUS FOR ASPIRATING SECRETED FLUIDS FROM A WOUND

[75] Inventors: Walter Beck, Obere Häslibachstr. 87, CH-8700 Küsnacht; Siegfried Berger, Wernau; Margrit Werner, Lion-Feuchtwanger-Str. 69, 6500 Mainz-Hechtsheim, all of Fed. Rep. of Germany

[73] Assignees: Walter Beck; Margrit Werner, both of Fed. Rep. of Germany

[21] Appl. No.: 798,845

[22] Filed: Nov. 18, 1985

[30] Foreign Application Priority Data

Nov. 16, 1984 [DE] Fed. Rep. of Germany ....... 3441891

[51] Int. Cl.⁴ ............................................ A61M 31/00
[52] U.S. Cl. ...................................... 604/54; 604/120
[58] Field of Search ............... 604/317, 318, 119, 120, 604/48, 49, 52–56, 22, 28, 320, 321, 18; 116/268, 270, 272; 73/714; 417/477; 141/2

[56] References Cited

U.S. PATENT DOCUMENTS

| 1,155,271 | 9/1915 | Philips | 604/318 |
| 3,429,313 | 2/1969 | Romanelli | 604/120 |
| 4,168,707 | 9/1979 | Douvas et al. | 128/305 |
| 4,274,411 | 6/1981 | Dotson, Jr. | 604/22 |
| 4,319,573 | 3/1982 | Whitlock | 604/323 |
| 4,384,580 | 5/1983 | Leviton | 604/320 |
| 4,468,226 | 8/1984 | Kurtz et al. | 604/318 |
| 4,561,807 | 12/1985 | Hilse et al. | 417/477 |

FOREIGN PATENT DOCUMENTS

| 2543185 | 2/1977 | Fed. Rep. of Germany . |
| 2851656 | 6/1979 | Fed. Rep. of Germany . |
| 2103187 | 8/1979 | Fed. Rep. of Germany . |
| 2820517 | 11/1979 | Fed. Rep. of Germany . |
| 2826033 | 12/1979 | Fed. Rep. of Germany . |
| 8010779 | 8/1980 | Fed. Rep. of Germany . |
| 2917332 | 11/1980 | Fed. Rep. of Germany ...... 604/318 |
| 3321151 | 12/1984 | Fed. Rep. of Germany . |

Primary Examiner—C. Fred Rosenbaum
Assistant Examiner—J. L. Kruter
Attorney, Agent, or Firm—Wigman & Cohen

[57] ABSTRACT

The present invention relates to a method and apparatus for aspiration of secreted fluids from a wound by means of a drain that is connected with a container by a tube, in which the container is a negative pressure, which decreases with the flow of secreted fluid, and regenerates from time to time to a selectable value. A closed system formed by the drain, the container and the tube connecting the two is supplemented for this purpose with a collection container and a second tube that connects the collection container with the container. The second tube has at least one section to which a tube pump can be applied. A clamp is provided in the line formed by the second tube between the container and the collection container.

10 Claims, 1 Drawing Figure

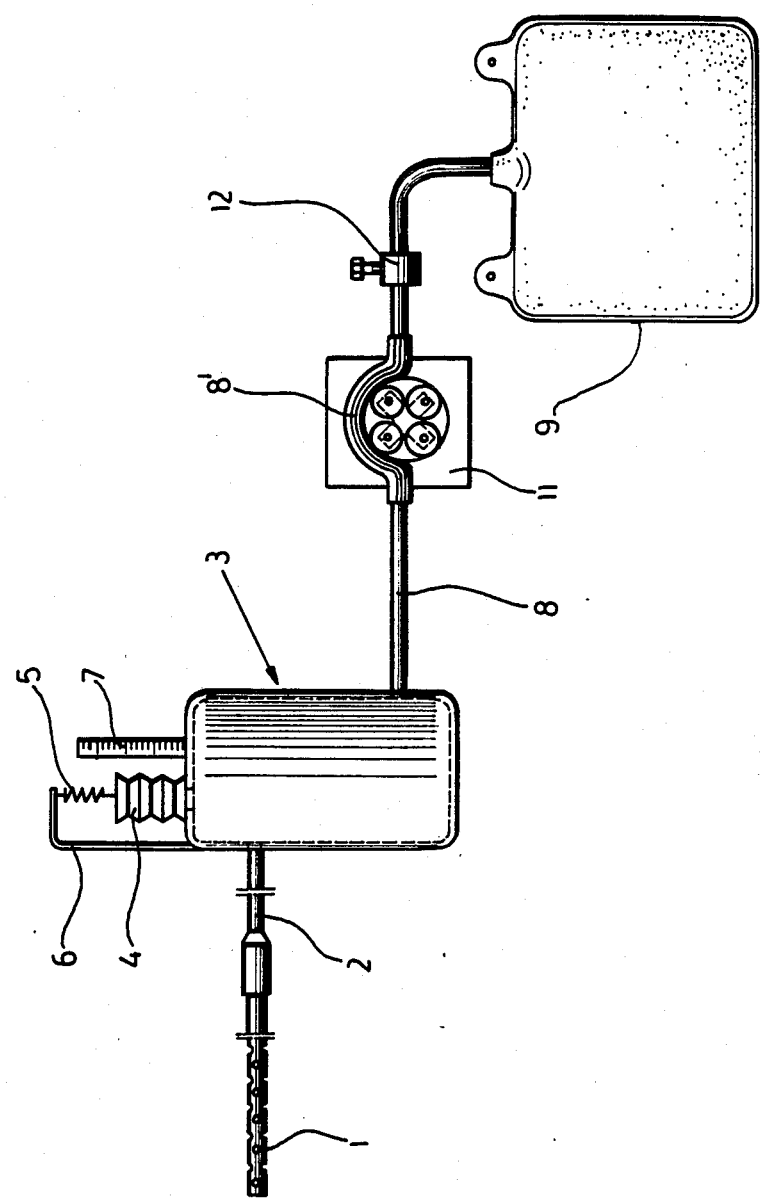

METHOD AND APPARATUS FOR ASPIRATING SECRETED FLUIDS FROM A WOUND

CROSS REFERENCE TO RELATED APPLICATION

This application is related to concurrently filed application entitled Method and Apparatus for Aspirating Secreted Fluids from a Wound, commonly assigned.

BACKGROUND OF THE INVENTION

The invention relates to a method for aspirating secreted fluids from a wound by means of a drain, which is connected to a container by a tube, in which container a negative pressure prevails, and to an apparatus for performing the method.

In the known methods of this type, the aspiration of the secreted fluids begins at maximum negative pressure, i.e., with maximum suction effect. The negative pressure, and therefore also the suction effect, decrease in accordance with the quantity of aspirated fluid. This decrease results from the fact that the negative pressure prevailing in the container drops as the secreted fluid aspirated into the container increases. In this known method it is not only problematical that the beginning suction effect may under certain circumstances be too high, but also and primarily that there is no possibility to adapt the suction effect to given requirements or to hold the suction effect almost constant over an extended period of time. Furthermore, in the known methods there is a danger of contamination at least whenever a change of containers is necessary, since the connection between the container and the tube connected to the drain must be opened for a change of containers.

OBJECTS AND SUMMARY OF THE INVENTION

The object of the invention is to provide a method for aspirating secreted fluids from a wound, which can be adaptable and also precludes any danger of contamination. Other objects will become apparent from the detailed description which follows.

Since the negative pressure in the container receiving the aspirated secreted fluids can be regenerated from time to time to a selectable value, the initially effective negative pressure need not be selected at a rate necessary to insure that the suction effect is present for as long as possible. To the contrary, it can be selected in accordance with the initially optimal value. Similarly, the negative pressure, is reduced by the secreted fluids arriving in the container, but can subsequently be brought back to the desired value at any desired point in time said desired value may be the same as the original value, lower or higher. In addition, the danger of contamination is precluded because the container can remain connected with the drain of the tube during the entire duration of secreted fluid aspiration, since the secreted fluid that has collected in the container can be led off during the regeneration of the negative pressure.

In the preferred embodiment the contents of the container are aspirated therefrom through a tube into a collection container, such that the tube leading to the collection container is subjected to the effect of a tube pump. In this manner it is assured that the system also remains completely closed during the regeneration phase. Because the aspiration of the contents of the container and the renewed setting of the negative pressure in the container need only take place from time to time, it is not necessary that the closed system be continuously combined with a tube pump. To the contrary, it is sufficient to subject the tube leading from the container to the collection container to the effect of a tube pump only during each regeneration phase. Then, several secreted fluid suction systems can be supplied with a single tube pump, which significantly reduces the expense.

A further object of the invention is to create an apparatus for performing the method according to the invention, which has no application problems and yet is so economical that it can be used here as a disposable system.

Because the present inventive apparatus retains the container in which a negative pressure prevails, the use of the apparatus according to the invention is entrusted to the personnel in hospitals and clinics. This alone significantly eases operation. The fact that from time to time a tube pump must be applied to the tube leading from the container to the collection container, does not cause any difficulty in practice. The operation is more simple than the known systems, because a container exchange is not necessary. If the tube pump is continuously connected with the second tube and has a form that assures that the second tube is blocked, the tube pump itself can form the blocking device. In other cases, however, a blocking device provided in addition to the tube pump is necessary in order to be able to block the second tube between the container and the tube container at the end of each regeneration process.

A negative pressure display device is necessary to determine the negative pressure prevailing in the system. In one preferred embodiment, this display device is provided on the container, because the apparatus can be combined therewith in a particularly simple manner. Preferably, this negative pressure display device consists of a folding bellows the inner chamber of which communicates with the inner chamber of the container, a return spring engaging on the folding bellows, and a scale on which the prevailing negative pressure can be read from the position of the folding bellows or also the length of the return spring. A negative pressure display device of this type is particularly advantageous to the extent that it is comprised only of simple, economical elements. The folding bellows can consist of rubber or plastic. The display device therefore can be thrown away together with the container after use. With a very large display range, to avoid a relatively long folding bellows and a relatively long return spring, it can be more advantageous to provide at least two negative pressure display devices of this type, which have different measurement ranges.

For cost reasons it is preferable to form the container as a bottle and the collection container as a bag. For the same reason a tube clamp can be provided as a blocking device.

BRIEF DESCRIPTION OF THE DRAWING

The invention is described in greater detail below with the aid of an exemplary embodiment of the apparatus according to the invention as illustrated in the drawing. The single drawing illustrates a partial view of the present invention.

DESCRIPTION OF A PREFERRED EMBODIMENT

A drain 1 formed in a known manner is connected by means of a first tube 2 with a rigid, plastic bottle 3. The support (not shown) of the bottle for the drain 2 is located near the cover that closes the top of the bottle 3. In the exemplary embodiment, this cover is provided with a single connection support with which one end of a folding bellows 4 is sealingly connected. However, a second connection support for a second folding bellows could also be present. The folding bellows 4, the inside of which communicates with the inner chamber of the bottle 3 via the supports, is connected with the end of a helical tensile spring 5 opposite the bottle 3, the other end of which is suspended on a holder 6 that is rigidly connected with the bottle 3. The spring 5 forms a return spring which seeks to stretch the folding bellows 4, which is generally made of rubber or plastic. A negative pressure in the bottle 3 causes the folding bellows 4 to shorten and the spring 5 to lengthen accordingly. The folding bellows 4 and the spring 5 thus together form a sensor for the level of the negative pressure in the bottle. In order to display the value of the negative pressure, a scale 7 is arranged adjacent the folding bellows 4, on which the length of the folding bellows 4 and the associated level of the negative pressure in the bottle 3 can be read. The scale 7, the folding bellows 4 and the helical spring 5 together with the holders 6 that hold them, therefore form a netative pressure display device.

Near the bottom of bottle 3 is a support (not shown) to which one end of a second tube 8 is connected. This second tube leads to a collection container 9, which in the exemplary embodiment is a bag and is advantageously selected so that it can receive the entire quantity of secreted fluid without having to be replaced. The system can thereby remain completely closed.

The second tube 8 has a section 8' made of silicone rubber which is intended for cooperation with a tube pump 11. Furthermore, in the area between the section 8' and the collection container 9, the second tube 8 is carrying a manually activatable tube clamp 12.

After the drain 1 has been introduced into the wound and the wound has been closed, the bottle 3 is evacuated by the tube pump 11 until the optimal negative pressure for the aspiration of the wound secreted fluids is achieved in the bottle 3. Then, the tube clamp 12 is closed and the tube pump 11 is turned off or removed entirely, so that it can be used elsewhere. Because of the increasing quantity of secreted fluid that collects in the bottle 3, the negative pressure in the inside of the bottle 3 decreases. This reduction in pressure can be read on the scale 7 because the spring 5 extends the folding bellows 4 accordingly.

As soon as the negative pressure in the bottle 3 has reached the permissible lower limit value, the tube pump 11 is reactivated in that it is turned on or applied to the section 8' of the tube 8 and then turned on. While the tube pump 11 operates, the tube clamp 12 must be open, so that the secreted fluid pumped from the bottle 3 can flow into the collection container 9. The aspiration of the secreted fluid from the bottle 3 has the result that the negative pressure in the bottle 3 again increases. As soon as the desired value is reached, which can be recognized from the scale 7, the tube clamp 12 is again closed, the tube pump 11 is turned off and, if desired, also separated from the section 8'. After the completion of the aspiration of the secreted fluids, all elements with the exception of the tube pump 11, are disposed of.

As seen from the described method steps, the negative pressure in the bottle 3 and thereby the suction effect can be held within any desired selectable range during the aspiration of the secreted fluids. In addition, the system, which is closed in a microbiological respect, consists of the drain 1, the first tube 2 and bottle 3, the second tube 8 and the connection container 9 do not need to be opened, so that no contamination danger arises.

Although only preferred embodiments, are specifically illustrated and described herein, it will be appreciated that many modifications and variations of the present invention are possible in light of the above teachings and within the purview of the appended claims without departing from the spirit and intended scope of the invention.

What we claim is:

1. A method for aspirating secreted fluids from a wound comprising the steps of:
    providing a drain connected to a first container by a first tube to form a closed system;
    providing a second container connected to said first container by a second tube;
    providing a tube pump and tube clamp on said second tube;
    inserting said drain into the wound and closing said wound;
    evacuating said first container by operating said tube pump to achieve a negative pressure in said first container;
    closing said tube clamp and stopping the operation of said tube pump;
    maintaining a negative pressure in said container;
    periodically regenerating the negative pressure in said first container as the secreted fluids flow into said first container to a predetermined value while maintaining said system closed during the regenration phase, wherein at least a portion of the content of the first container is aspirated and pumped into said second container during the regeneration phase, and wherein the content of said first container aspirated therefrom is led through said second tube into said second container, said second tube being subjected to the effect of said operating tube pump and said tube clamp being open whereby said collection takes place in a closed system.

2. An apparatus for aspirating secreted fluids from a wound comprising:
    a drain connected to a first evacuatable container by a first tube forming a close system;
    a second collection container and a second tube connecting same with said first evacuatable container and a tube pump acting on a section of said second tube between said containers. and clamp means for blocking said second tube located at a point lying between said first evacuatable container and said second collection container, wherein said drain, said first tube, said first evacuatable container, said second tube and said second collection container are fluidly connected together to form a closed system, and said tube pump and clamp means are disposed outside said closed system.

3. The apparatus according to claim 2, further including a negative pressure display device associated with said first evacuatable container.

4. The apparatus according to claim 3, wherein said negative pressure display device has at least one folding bellows provided at the outside of said first evacuatable container, the inside of which bellows communicates with the inside of said first evacuatable container, a return spring which engages on the folding bellows, and a scale.

5. The apparatus according to claim 2 wherein the first container is formed as a bottle and the second collection container is formed as a bag.

6. The apparatus according to claim 2 wherein said clamp means is a tube clamp.

7. The apparatus according to claim 2, wherein said clamp means is said tube pump.

8. The apparatus according to claim 2, wherein the entire closed system comprises disposable elements.

9. The apparatus according to claim 2, wherein said second tube acted on by said tube pump is flexible along the portion acted on.

10. The apparatus according to claim 2, including means for evacuating said evacuatable container.

* * * * *